(12) United States Patent
Hong et al.

(10) Patent No.: US 11,959,113 B2
(45) Date of Patent: Apr. 16, 2024

(54) PRODUCTION PROCESS AND APPLICATION OF FERMENTED TAPIOCA STARCH FOR BAKING

(71) Applicant: Jiangnan University, Wuxi (CN)

(72) Inventors: Yan Hong, Wuxi (CN); Qiaoting Qi, Wuxi (CN); Zhengbiao Gu, Wuxi (CN); Li Cheng, Wuxi (CN); Zhaofeng Li, Wuxi (CN); Caiming Li, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 733 days.

(21) Appl. No.: 17/108,382

(22) Filed: Dec. 1, 2020

(65) Prior Publication Data
US 2021/0087597 A1    Mar. 25, 2021

Related U.S. Application Data

(63) Continuation of application No. PCT/CN2019/086179, filed on May 9, 2019.

(30) Foreign Application Priority Data

Apr. 1, 2019    (CN) .......................... 201910256703.3

(51) Int. Cl.
  *C12P 19/04*    (2006.01)
  *A21D 2/18*    (2006.01)
(52) U.S. Cl.
  CPC .............. *C12P 19/04* (2013.01); *A21D 2/186* (2013.01)

(58) Field of Classification Search
  CPC ...................................................... C12P 19/04
  See application file for complete search history.

(56) References Cited

U.S. PATENT DOCUMENTS

2013/0129864 A1    5/2013  Brandt et al.

FOREIGN PATENT DOCUMENTS

| CN | 102304480 A | 1/2012 |
| CN | 105076900 A | 11/2015 |

OTHER PUBLICATIONS

Zhao. Effects of lactic acid bacteria and molasses on fermentation dynamics, structural and nonstructural carbohydrate composition and in vitro ruminal fermentation of rice straw silage. Anim Biosci 2019;32(6):783-791. Published online: Nov. 27, 2018.*

(Continued)

*Primary Examiner* — Yong D Pak
(74) *Attorney, Agent, or Firm* — IPRO, PLLC

(57) ABSTRACT

The disclosure discloses a production process and application of fermented tapioca starch for baking, and belongs to the fields of starch deep processing and food processing and production. The disclosure develops a production method of the fermented tapioca starch for baking. The method includes simple steps and greatly shortens a process cycle. By using tapioca starch as a main raw material and adding a specific amount of carbon source and a specific strain, under the action of fermentation and illumination in cooperation, the structure of the starch is improved. By adding the fermented tapioca starch, the effects of increasing the size of gluten-free Mochi bread, increasing pores of the bread and improving the texture and taste of the bread are realized.

9 Claims, 5 Drawing Sheets

(56) References Cited

OTHER PUBLICATIONS

Putri. W.D.R. et al. "Effect of Biodegradation by Lactic Acid Bacteria on Physical Properties of Cassava Starch" International Food Research Journal, vol. 18, No. (3), Dec. 31, 2011 (Dec. 31, 2011).

Marcon, M.J.A. et al. "Effect of the Improved Fermentation on Physicochemical Properties and Sensorial Acceptability of Sour Cassava Starch" Brazilian Archives of Biology and Technology, vol. 50, No. (6), Nov. 30, 2007 (Nov. 30, 2007).

Du, Jing et al. "Enzyme Assisted Fermentation of Potato Pulp an Effective Way to Reduce Water Holding Capacity and Improve Drying Efficiency" Food Chemistry, Vol. vol. 258, Mar. 7, 2018 (Mar. 7, 2018).

Marcon. M.J.A. et al. "Expansion Properties of Sour Cassava Starch (*Polvilho azedo*): Variables Related to its Practical Application in Bakery" Starch, vol. vol. 61, Dec. 31, 2009 (Dec. 31, 2009).

Wan Jing-jing et al. "Effect of Lactic Acid Bacterial Fermentation on the Physico-chemical and Thermodynamic Properties of Oat Starch" Food Science,2010, vol. 31, No. 19.

\* cited by examiner

PRODUCTION PROCESS AND APPLICATION OF FERMENTED TAPIOCA STARCH FOR BAKING

TECHNICAL FIELD

The disclosure particularly relates to a production process and application of fermented tapioca starch for baking, and belongs to the fields of starch deep processing and food processing and production.

BACKGROUND

Celiac disease is a type of autoimmune deficiency disease. Gluten (gluten protein) in wheat and other grains can induce autoimmunity, leading to intestinal mucosal lesions in patients with clinical manifestations of diarrhea, anemia, osteoporosis and other symptoms. The incidence rate of celiac disease has reached 1% in European and American countries. In recent years, reports on celiac disease have been increasing year by year in China. The gluten-free market is on the rise as the economy grows and people pay more attention to their health. The United States, Japan, the European Union and other countries strictly regulate the amount of gluten in food. The Codex Alimentarius Commission (CAC) of WHO/FAO defines gluten-free food as the food that has not been processed by using wheat, barley, rye, oats or their hybrid varieties and does not contain more than 20 mg/kg of gluten. Currently, there are no relevant regulations on gluten-free food in China, but it is a field that deserves attention.

At present, for gluten-free bread, the network structure of bread is enhanced under the action of forming a network with gluten or related colloids and the action of gelatinization of starch. It is difficult to form a network structure for gluten-free products due to the lack of gluten in raw materials, which results in weak water holding capacity, poor air holding capacity, dough looseness, dough formation difficulty, internal pore unevenness of bread, easy collapse and lack of toughness. Finished products of gluten-free bread tend to have a hard texture, small network pores, a rough taste, and a higher ageing speed. Fermented tapioca starch has excellent swelling power, and may be made into completely gluten-free bread without fermentation under the action of gelatinization of starch, thereby saving time and space cost.

Fermented tapioca starch (polvilho azedo) is a traditional food raw material mainly used in Brazil and other South American countries to make cheese bread (pão do queijo). A traditional preparation process of the fermented tapioca starch includes cleaning, peeling, grinding and smashing, underwater squeezing and agglomerating, slag removal, natural fermentation, sun drying and other steps. A traditional fermentation method of natural fermentation includes: putting tapioca starch pulp in a fermentation tank coated with paint to stand, covering the fermentation tank with a 4 cm water layer for standing and fermenting, and determining an end time of fermentation by judging the state of foam above the water layer through experience. Natural fermentation mainly goes through three stages: the stage of non-severe microorganisms, the stage of dominant lactic acid bacteria and the stage of yeast and saprophytic bacteria. At the stage of non-severe microorganisms, *Escherichia, Alkaligenes, Micrococcus* and *Pseudomonas* are mainly produced, and the dissolved oxygen concentration decreases rapidly. At this stage, it is detected that *Bacillus* produces amylolytic enzyme, granule starch is enzymatically digested to provide a carbon source for bacteria at the second stage. At the same time, present non-symbiotic nitrogen-fixing bacteria provides a nitrogen source for the bacteria at the second stage. The stage of dominant lactic acid bacteria mainly involves the development of aerobic microorganisms, facultative or strictly anaerobic bacteria for lactic acid, acetic acid, butyric acid and propionic acid fermentation. In cold regions, the fermentation speed is lower and lactic acid bacteria are dominant, while in hot regions, the fermentation speed is faster and butyric acid is dominant. The stage of yeast and saprophytic bacteria includes: the stage of synthesizing aromatic compounds by the yeast and the stage of producing unpleasant flavor by the saprophytic bacteria later. Therefore, it is necessary to judge an end time of natural fermentation by experience and stop fermentation in time to prevent putrid bacteria from producing unpleasant flavor and thus affecting product quality. At the same time, the natural fermentation cycle is long, which is generally 15-90 days.

In order to enter the stage of dominant lactic acid bacteria quickly, some manufacturers choose an artificial acid addition mode, but they are unable to produce fermented tapioca starch with an excellent expansion property, which indicates that only relying on acidity improvement, fermentation quality may not be effectively improved. In addition, some manufacturers choose to recycle fermentation waste liquor by settling it to remove insoluble relevant impurities and then adding it to fresh tapioca pulp. This method may obviously shorten the fermentation time and produce excellent fermented tapioca starch. However, there is a potential hazard of toxin accumulation in the recycled fermentation liquor, and there are great potential safety hazards in mixed strains. By observing the thickness of foam on an upper layer in a fermentation system and measuring an acidity of the fermentation liquor, enterprises determine the production time of products by experience. In production of enterprises, due to a difference of sizes of fermentation systems, the presence time of foam on an upper layer in a larger fermentation system is obviously longer than that in a smaller fermentation system, and there is a considerable difference in the start time and end time of fermentation. In a process of fermentation, starch deposits at the bottom to form substances similar to semi-solids, a water seal isolates oxygen at the top, in the initial time, oxygen in the system is quickly consumed, anaerobic fermentation in the system is generated from top to bottom, and bubbles rise to form foam on the surface. When the system becomes larger, the thickness of a starch layer increases, the whole anaerobic fermentation time is prolonged, and the duration of foam is prolonged, while an acidity of the water seal layer at the top of the starch layer is already low. Conditions of the fermentation process are not up to standard, the product quality fluctuates, and the product stability is poor.

SUMMARY

The disclosure discloses a preparation method of fermented tapioca starch for baking. The preparation method includes:

(1) mixing a carbon source with water to prepare a fermentation medium; and (2) adding tapioca starch to form starch milk, and inoculating the starch milk with *Lactobacillus plantarum* CCTCC M2017138 for fermentation to obtain the fermented tapioca starch.

In one embodiment of the disclosure, the *L. plantarum* CCTCC M2017138 was disclosed on Mar. 7, 2018 in an article (Enzyme assisted fermentation of potato pulp: An effective way to reduce water holding capacity and improve drying efficiency. Jing Du. Food Chemistry. 258 (2018), 118-123).

In one embodiment of the disclosure, an initial mass concentration of the carbon source in the fermentation medium in step (1) is 0.1-10 g/100 g.

In one embodiment of the disclosure, the carbon source is a carbon source containing monosaccharide.

In one embodiment of the disclosure, the carbon source includes molasses, corn steep liquor, glucose and the like.

In one embodiment of the disclosure, a mass concentration of the tapioca starch in the starch milk in step (2) is 30-70 g/100 g.

In one embodiment of the disclosure, an inoculum size of the L. plantarum in step (2) is 1-20% of a total mass of the starch milk, equivalent to 1-30% of a dry basis mass of the starch.

In one embodiment of the disclosure, inoculating with the L. plantarum for fermentation in step (2) is inoculating the starch milk with a L. plantarum seed solution for fermentation.

In one embodiment of the disclosure, a concentration of the L. plantarum in the L. plantarum seed solution is $1.0 \times 10^9$-$7.0 \times 10^9$ CFU/mL.

In one embodiment of the disclosure, a culture medium of the L. plantarum seed solution is a Lactic acid bacteria culture medium (MRS broth).

In one embodiment of the disclosure, a preparation process of the L. plantarum seed solution includes: preparing a Lactic acid bacteria agar plate, streaking the plate with a strain preservation tube for culturing for 24 h at 37° C., and taking out the plate to be stored in a refrigerator at 4° C.; and picking a single colony from the plate to inoculate the Lactic acid bacteria culture medium (liquid) with the single colony.

In one embodiment of the disclosure, the L. plantarum seed solution has a culture temperature of 37° C. and a culture time of 10-20 h.

In one embodiment of the disclosure, in step (2), a fermentation temperature is 30-40° C., and a fermentation time is 12-120 h.

In one embodiment of the disclosure, the method further includes the step: performing illumination after fermentation ends.

In one embodiment of the disclosure, an illumination time is 6-72 h under the condition of an average illumination intensity of 100,000-300,000 lux.

In one embodiment of the disclosure, a water content of a tapioca starch basis before illumination is 30-60 g/100 g.

In one embodiment of the disclosure, step (1) further includes sterilizing the fermentation medium.

In one embodiment of the disclosure, a sterilizing mode includes: high-temperature and high-pressure sterilizing for 20-30 min at a temperature of 115-121° C., and a pressure of 0.1-0.3 MPa.

In one embodiment of the disclosure, in step (2), the starch is added after the fermentation medium is sterilized and cooled to 20-50° C. to form the starch milk.

In one embodiment of the disclosure, step (2) further includes washing after fermentation ends, where a pH after washing is 3.5-7.

In one embodiment of the disclosure, the method specifically includes:

(1) mixing a certain amount of carbon source with water, and performing sterilizing and cooling to prepare a fermentation medium;

(2) adding a certain amount of starch to form starch milk, injecting the starch milk into a fermentation tank, and inoculating with a certain amount of activated L. plantarum seed solution for fermentation;

(3) washing the final starch milk to a certain pH after fermentation ends, and adjusting the starch milk to a certain water content; and (4) performing sunlight drying to obtain fermented tapioca starch.

The disclosure further discloses the fermented tapioca starch for baking, where the starch is prepared through the method above.

The disclosure further discloses bread, wherein the bread has a formula including the fermented tapioca starch.

The disclosure further discloses application of the fermented tapioca starch to the field of baking.

The method for producing the fermented tapioca starch for baking of the disclosure is simple in step and greatly shortens the process cycle; and by using the tapioca starch as a main raw material and adding a specific amount of carbon source and a specific strain, under the action of fermentation and illumination in cooperation, the structure of the starch is improved. By adding the fermented tapioca starch, the effects of increasing the size of gluten-free Mochi bread, increasing pores of the bread and improving the texture and taste of the bread are realized. The method of the disclosure may produce the product with an excellent expansion property through fermentation of the L. plantarum by comparing expansion properties of the fermented tapioca starch under different fermentation conditions and fermentation strains. Due to fermentation of the L. plantarum, the viscosity of the tapioca starch is reduced, the setback property is reduced, the gelatinization temperature is lowered, the swelling capacity and the water holding capacity of the starch are increased, physical and chemical properties and a crystal structure of the tapioca starch are changed, and the gelatinization action of the starch is facilitated, which makes good gluten-free bread. The defects of a poor gas holding capacity, a poor water holding capacity, a rough taste, a poor texture structure and the like of the gluten-free bread are overcome, and the aim of improving the texture of the gluten-free bread is realized.

The disclosure adopts a specific single-strain fermentation process, it has a short production cycle so as to obtain the fermented tapioca starch within 5 days, and it is low in energy consumption and easy to operate. Toxin hazards caused by a plurality of mixed strains are eliminated, leading to a safe and uniform product quality. The method of the disclosure increases the utilization rate of a culture medium and ensures a product quality and benefits by reasonably using physical and chemical changes and reasonably adding ingredients.

The tapioca starch processed through fermentation and illumination by the method of the disclosure is changed in its structural properties, specifically reflected in reduction of a gelatinization viscosity from a raw starch high viscosity of 1,650 mPa·s to 1,100 mPa·s and reduction of a setback value from a raw starch setback value of 500 mPa·s to 150 mPa·s, thereby replacing or partly replacing relevant hydrophilic colloids to improve the gluten-free bread; and meanwhile, the expansion property of the tapioca starch is increased to be 1.5-2 times an original expansion property thereof, its gel structural strength is improved, collapse is reduced and pores are even.

DETAILED DESCRIPTION

Figure 1:
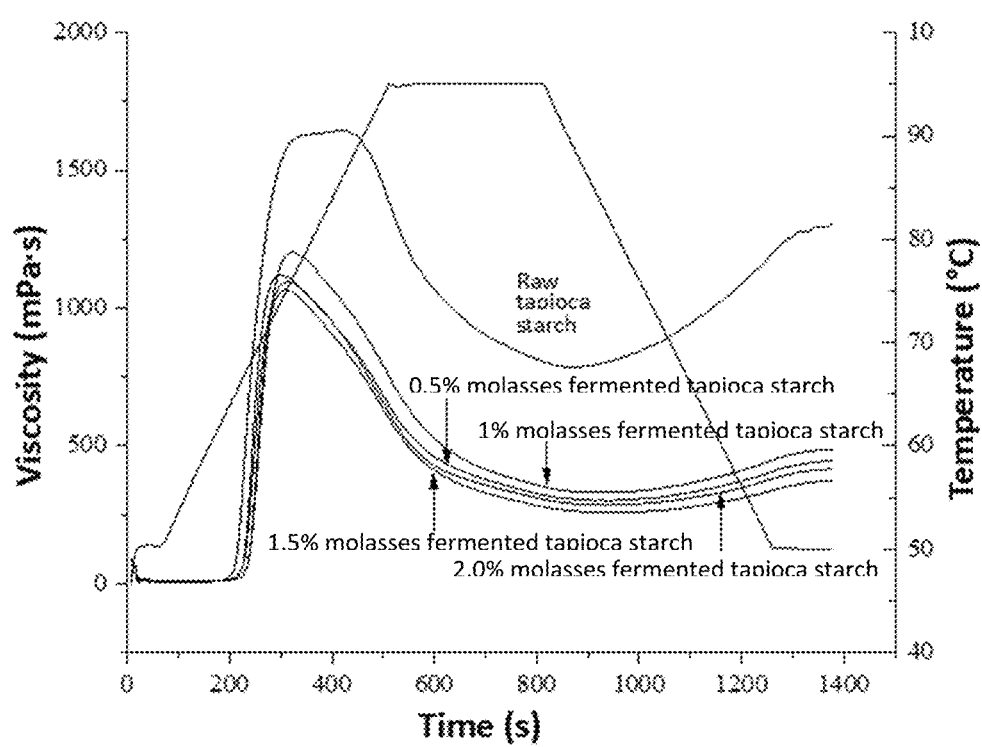
FIG. 1 shows gelatinization property curves of fermented tapioca starch obtained from different use amounts of carbon source in Example 2 and raw starch thereof.
Figure 2:
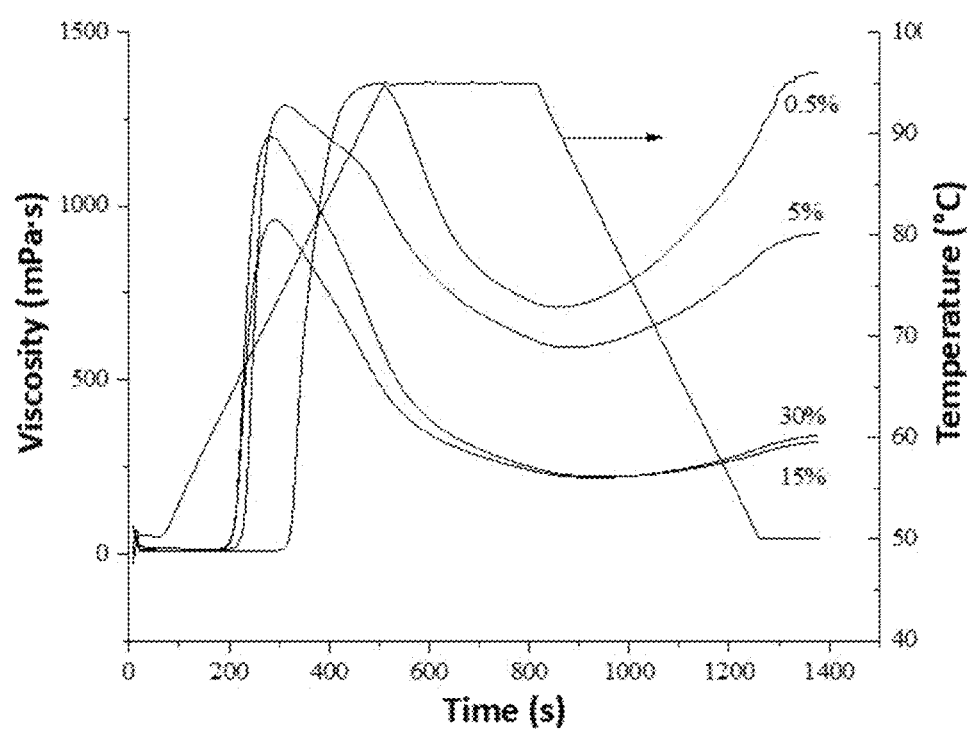
FIG. 2 shows gelatinization property curves of fermented tapioca starch obtained from different inoculum sizes of strain in Example 3 and raw starch thereof.
Figure 3:
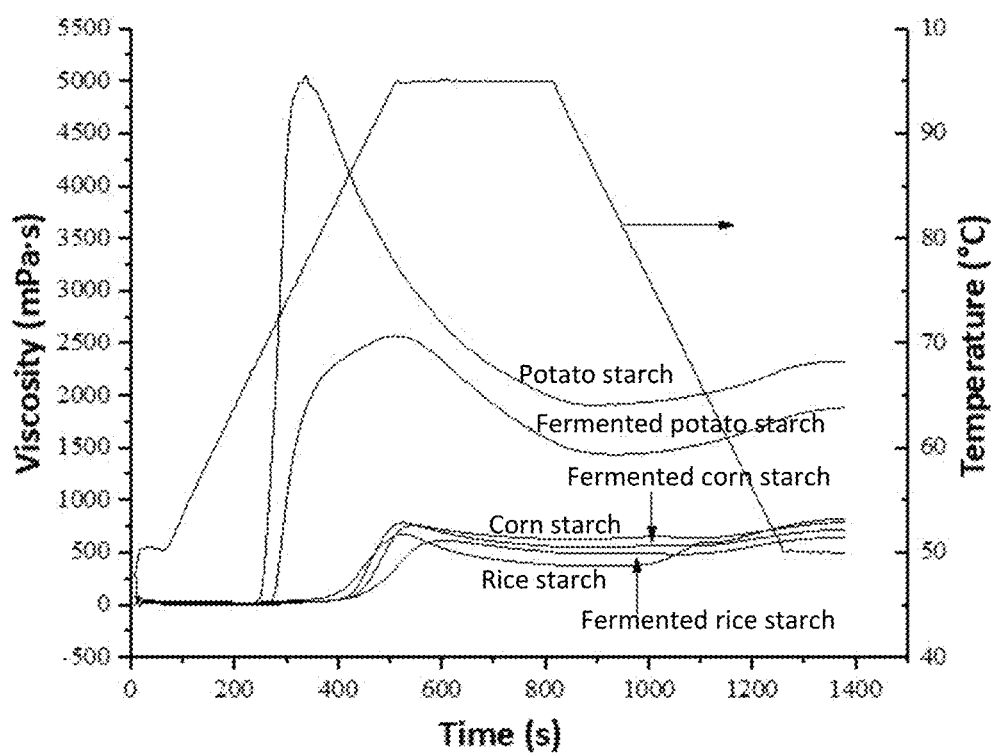
FIG. 3 shows gelatinization property curves of fermented starch from different sources and raw starch.
Figure 4:
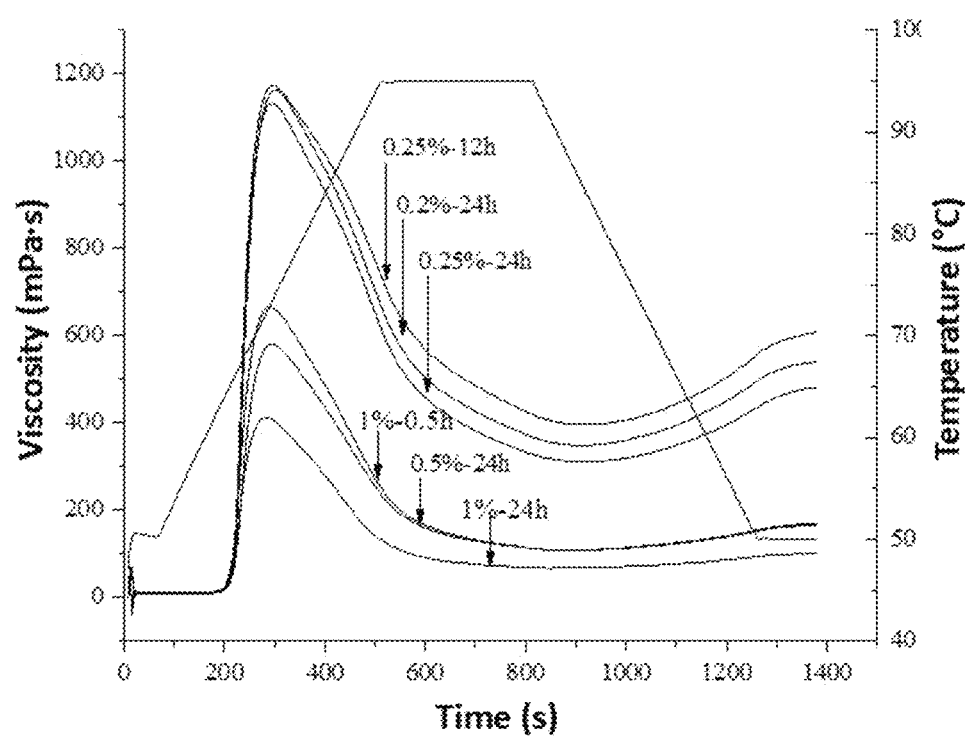
FIG. 4 shows gelatinization property curves of tapioca starch obtained by acid addition.
Figure 5:
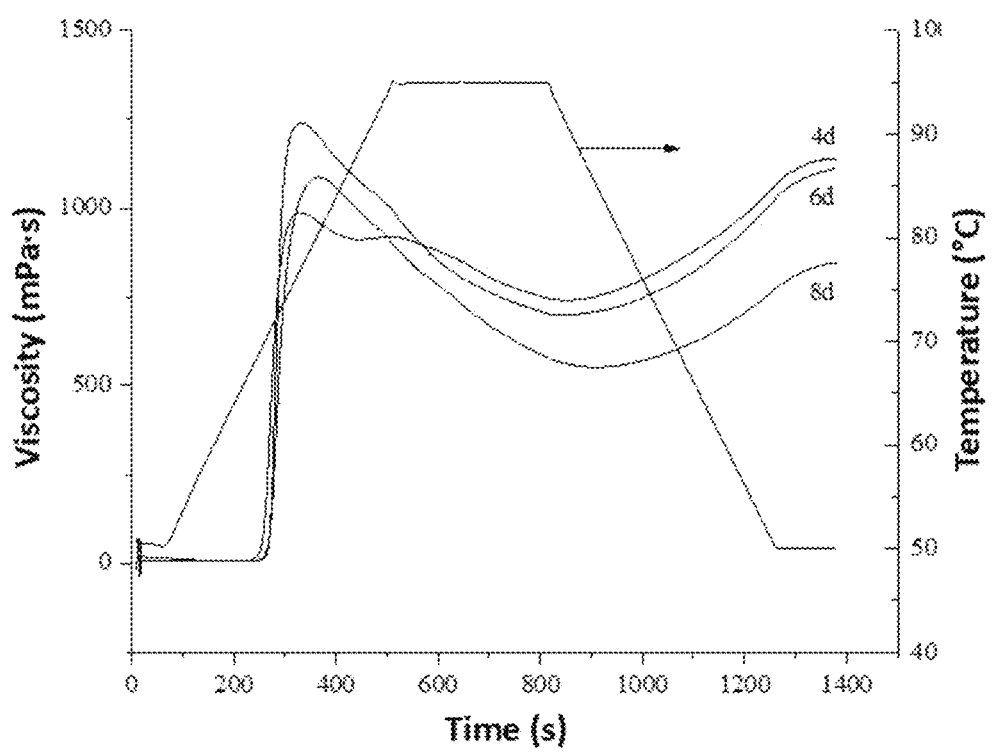
FIG. 5 shows gelatinization property curves of fermented tapioca starch obtained by natural fermentation for different times.

The implementation scheme of the disclosure is described in detail with reference to Examples as follows. If no specific conditions are indicated in Examples, conventional conditions are adopted. Agents and instruments that are used have no clear indication of manufacturers are all conventional products.

A measurement method for types and contents of organic acids in fermentation liquor comprises the steps: separating the organic acids in the fermentation liquor by a C-18 reverse chromatographic column, and detecting contents of malic acid, lactic acid, formic acid, acetic acid, citric acid, succinic acid, fumaric acid, propionic acid, butyric acid, tartaric acid and ascorbic acid.

A measurement method for a gelatinization property of starch comprises the steps: weighing a certain mass of corn acidified starch sample to be evenly mixed with deionized water in an RVA aluminum specimen box to prepare a suspension with a total mass percentage of 6% (based on a dry basis); performing measurement according to Standard 2 of a stipulated method of American Association of Cereal Chemists (AACC) by steps of heat preserving for 1 min at 50° C., heating to 95° C. at a speed of 6° C./min, heat preserving for 5 min, cooling to 50° C. at a speed of 6° C./min and heat preserving for 2 min; and performing viscosity measurement at a stirring rate of 960 r/min within the first 10 s and then a stirring rate of 160 r/min.

Peak viscosity: rapid viscosity analyzer (RVA), starch mass concentration of 6%.

An expansion property of starch is tested by the following steps: evenly kneading 50 g of starch with 40 mL of boiling water, cutting the dough into pieces with a weight of 10 g, shaping the pieces into a flat and round shape, and baking the pieces with upper fire and lower fire for 20 min at 200° C.; measuring sizes after baking by a millet replacement method in triplicate; and obtaining the expansion property (mL/g) according to sizes after baking/original mass.

The method of the disclosure may be implemented generally as follows.

Fermented tapioca starch for baking and a production method thereof are provided. The production method comprises the steps:

1, preparing a fermentation medium with a content of 0.1-10 g/100 g from molasses (based on the content of available glucose), and performing high-temperature and high-pressure sterilizing, where the temperature range is controlled to be 115-121° C., the pressure range is controlled to be 0.1-0.3 MPa, and the sterilizing time is controlled to be 20-30 min;

2, obtaining a culture medium of a seed solution as a conventional culture medium that is the most suitable for the strain in this field, which is a Lactic acid bacteria culture medium (MRS broth), where the culture temperature is 30-40° C., the culture time is 10-20 h, and the concentration of Lactic acid bacteria in the culture medium is $1.0 \times 10^9$-$7.0 \times 10^9$ CFU/mL, and after cooling the fermentation medium to 20-50° C., adding tapioca starch under a clean environment at an addition amount of 30-70% of the fermentation medium, stirring to prepare starch milk, and transferring the cultured seed solution into the fermentation medium at an inoculum size of 1-20% of the starch milk (1-30% of the dry basis mass of the starch) at a fermentation temperature of 30-40° C. for a fermentation time of 12-120 h;

3, washing the starch milk to a pH of 3.5-7 after fermentation ends, and adjusting a water content of a fermented tapioca starch basis to 30-60%; and 4, flat spreading the starch milk with an adjusted water content on a drying container at an average illumination intensity of 100,000-300,000 lux for an illumination time of 6-72 h.

Example 1

(1) A fermentation medium with a content of 0.5 g/100 g is prepared from molasses (based on the content of available glucose), and the fermentation medium is sterilized for a sterilizing time of 20 min under conditions of a high temperature (115° C.) and a high pressure (0.2 MPa).

(2) A seed solution with a L. plantarum concentration of $4.2 \times 10^9$ CFU/mL is obtained with a L. plantarum culture medium (MRS broth) as a seed culture medium and L. plantarum (CCTCC M2017138) as a strain at a culture temperature of 37° C. for a culture time of 12 h. After the fermentation medium is cooled to 25° C., tapioca starch is added under a clean environment at an addition amount of 50% of a mass of the fermentation medium and stirred to prepare starch milk, and the seed solution is transferred into the fermentation medium at an inoculum size of 10% of a mass of the starch milk at a fermentation temperature of 37° C. for a fermentation time of 96 h.

(3) The starch milk is washed to a pH of 5 of the starch milk after fermentation ends, and the water content of a fermented tapioca starch basis is adjusted to 50%.

(4) The starch milk with adjusted water content is flat spread on a drying container at an average illumination intensity of 150,000 lux for an illumination time of 8 h to obtain fermented tapioca starch, where the production time of the whole process is 5 d.

Example 2

With reference to Example 1, fermented tapioca starch is prepared by changing an addition amount of molasses (based on the content of available glucose) to 0 g/100 g, 1.0 g/100 g, 1.5 g/100 g and 2.0 g/100 g respectively and keeping other conditions unchanged. The production time of each whole process is 5 d. Property results of obtained products are shown in Table 1, Table 2 and Table 3.

Gelatinization viscosity properties of the fermented tapioca starch obtained from different use amounts of carbon source are measured, and results are shown in Table 1. It is known from Table 1 that compared with raw starch, tapioca starch presents obvious drops in peak viscosity, trough viscosity, final viscosity and setback value after fermentation and illumination from 1,651 mPa·s, 796.5 mPa·s, 1,301.0 mPa·s and 504.5 mPa·s to about 1,100 mPa·s, 300 mPa·s, 450 mPa·s and 150 mPa·s respectively. The fermented tapioca starch obtained from different use amounts of carbon source presents small changes in breakdown value, with a drop of about 10-30 mPa·s. It is known from Table 3 by comparison that when the peak viscosity is 1,100-1,200 mPa·s, the expansion property of the starch is on the rise.

TABLE 1

Measurement of gelatinization viscosity properties of fermented tapioca starch obtained from different use amounts of carbon source

| Addition amount of molasses (%) | Peak viscosity (mPa·s) | Trough viscosity (mPa·s) | Breakdown value (mPa·s) | Final viscosity (mPa·s) | Setback value (mPa·s) |
|---|---|---|---|---|---|
| 0.0 | 1651.0 ± 7.1 | 796.5 ± 16.3 | 854.5 ± 9.2 | 1301.0 ± 8.5 | 504.5 ± 24.8 |
| 0.5 | 1120.5 ± 2.1 | 284 ± 24.0 | 836.5 ± 21.9 | 423.5 ± 31.8 | 139.5 ± 7.8 |
| 1.0 | 1198.0 ± 5.7 | 328.5 ± 2.1 | 869.5 ± 3.5 | 485.5 ± 2.12 | 157.0 ± 0.0 |
| 1.5 | 1119.5 ± 34.6 | 295.5 ± 16.3 | 824.0 ± 18.4 | 433.0 ± 24.0 | 137.5 ± 7.8 |
| 2.0 | 1057.5 ± 12.0 | 231.0 ± 36.8 | 826.5 ± 24.7 | 333.0 ± 58.0 | 102.0 ± 21.2 |

Contents of organic acids in fermentation liquor from a fermentation system with different use amounts of carbon source added are measured, and results are shown in Table 2. It is known from Table 2 and Table 3 that when a lactic acid concentration reaches 9,000-10,500 mg/L, the starch has an expansion property close to 6 mg/L and presents an excellent baking property. It is known from Table 3 that when an addition amount of molasses is 1.0 g/100 g, the expansion property is the best, when the addition amount of molasses is less than 1.0 g/100 g, the expansion property is on the rise, and as the addition amount of molasses increases, the expansion property drops instead.

TABLE 2

Measurement of types and contents of organic acids in fermentation liquor obtained from different use amounts of carbon source

| Addition amount of molasses (%) | Tartaric acid (mg/L) | Oxalic acid (mg/L) | Lactic acid (mg/L) | Citric acid (mg/L) | Succinic acid (mg/L) | Butyric acid (mg/L) |
|---|---|---|---|---|---|---|
| 0.5 | 34 ± 8 | 18 ± 6 | 3415 ± 148 | 7 ± 4 | 203 ± 23 | 928 ± 46 |
| 1.0 | 59 ± 10 | 20 ± 4 | 9097 ± 302 | 224 ± 13 | 121 ± 34 | 2354 ± 125 |
| 1.5 | 54 ± 5 | 19 ± 3 | 10359 ± 215 | 93 ± 3 | 288 ± 12 | 1817 ± 96 |
| 2.0 | 57 ± 3 | 31 ± 12 | 9083 ± 321 | 26 ± 16 | 182 ± 20 | 860 ± 34 |

Expansion properties of the fermented tapioca starch obtained from different use amounts of carbon source are measured, and results are shown in Table 3.

TABLE 3

Measurement of expansion properties of fermented tapioca starch obtained from different use amounts of carbon source

| | Addition amount of molasses (%) | | | | |
|---|---|---|---|---|---|
| | 0.0 | 0.5 | 1.0 | 1.5 | 2.0 |
| Expansion property (mL/g) | 3.37 ± 0.16 | 4.17 ± 0.26 | 6.52 ± 0.35 | 6.18 ± 0.50 | 5.85 ± 0.34 |

Example 3

(1) A fermentation medium with a content of 1.0 g/100 mL is prepared from molasses (based on the content of available glucose), and the fermentation medium is sterilized for a sterilizing time of 20 min under conditions of a high temperature (115° C.) and a high pressure (0.2 MPa).

(2) A seed solution with a *L. plantarum* concentration of $4.2 \times 10^9$ CFU/mL is obtained with a lactic acid bacteria culture medium (MRS broth) as a seed solution culture medium and *L. plantarum* (CCTCC M2017138) as a strain at a culture temperature of 37° C. for a culture time of 12 h. After the fermentation medium is cooled to 25° C., tapioca starch is added under a clean environment at an addition amount of 50% of a mass of the fermentation medium and stirred to prepare starch milk, and the cultured seed solution is transferred into the fermentation medium at an inoculum size of 0.5%, 5%, 15% and 30% of a mass of the starch milk instead at a fermentation temperature of 37° C. for a fermentation time of 96 h.

(3) The starch milk is washed to a pH of 5 after fermentation ends, and the water content of a fermented tapioca starch basis is adjusted to 50%.

(4) The starch milk with adjusted water content is flat spread on a drying container at an average illumination intensity of 150,000 lux for an illumination time of 8 h to obtain fermented tapioca starch.

Gelatinization viscosity properties of the fermented tapioca starch obtained from different inoculum sizes of strain are measured, and results are shown in Table 4. It is known from Table 4 that when the inoculum size is 0.5%, fermentation is quite slow, the gelatinization property of the obtained fermented tapioca starch does not change greatly compared with raw starch, and the expansion property of the starch slightly increases. When the inoculum size is increased to 30%, the viscosity of the obtained starch changes excessively, resulting in the drop of the expansion property of the starch. When the inoculum size is 10-15%, the obtained starch has a high expansion property within a proper viscosity range of 1,100-1,200 mPa·s. To sum up, it is economical and reasonable to make the inoculum size of a fermentation system at 10%.

TABLE 4

Measurement of gelatinization viscosity properties of fermented tapioca starch obtained from different inoculum sizes of strain

| Inoculum size of strain (%) | Peak viscosity (mPa · s) | Trough viscosity (mPa · s) | Breakdown value (mPa · s) | Final viscosity (mPa · s) | Setback value (mPa · s) |
|---|---|---|---|---|---|
| 0.5 | 1364 ± 15.5 | 653 ± 79.2 | 711 ± 94.8 | 1255 ± 182.4 | 602 ± 103.2 |
| 5 | 1282.5 ± 10.7 | 584 ± 14.1 | 698.5 ± 3.5 | 905.5 ± 20.5 | 321.5 ± 6.36 |
| 15 | 1180.5 ± 26.2 | 240 ± 26.8 | 940.5 ± 53.0 | 358 ± 50.9 | 118 ± 24.0 |
| 30 | 963 ± 2.8 | 222.5 ± 6.4 | 740.5 ± 3.5 | 343 ± 2.8 | 120.5 ± 3.5 |

Expansion properties of fermented tapioca starch obtained from different inoculum sizes of strain are measured, and results are shown in Table 5.

TABLE 5

Measurement of expansion properties of fermented tapioca starch obtained from different inoculum sizes of strain

| | Inoculum size of strain (%) | | | |
|---|---|---|---|---|
| | 0.5 | 5 | 15 | 30 |
| Expansion property (mL/g) | 4.24 ± 0.56 | 5.23 ± 0.87 | 6.08 ± 0.34 | 5.34 ± 0.40 |

Example 4

(1) A fermentation medium with a content of 0.5 g/100 mL is prepared from molasses (based on the content of available glucose), and the fermentation medium is sterilized for a sterilizing time of 20 min under conditions of a high temperature (115° C.) and a high pressure (0.2 MPa).

(2) A seed solution with a L. plantarum concentration of $4.2 \times 10^9$ CFU/mL is obtained with a lactic acid bacteria culture medium (MRS broth) as a seed solution culture medium and L. plantarum (CCTCC M2017138) as a strain at a culture temperature of 37° C. for a culture time of 12 h.

After the fermentation medium is cooled to 25° C., starch such as potato starch, rice starch and corn starch instead is added under a clean environment at an addition amount of 50% of a mass of the fermentation medium and stirred to prepare starch milk, and the cultured seed solution is transferred into the fermentation medium at an inoculum size of 10% of a mass of the starch milk at a fermentation temperature of 37° C. for a fermentation time of 96 h.

(3) The starch milk is washed to a pH of 5 after fermentation ends, and the water content of a fermented tapioca starch basis is adjusted to 50%.

(4) The starch milk with adjusted water content is flat spread on a drying container at an average illumination intensity of 150,000 lux for an illumination time of 8 h to obtain fermented tapioca starch, where a production time of the whole process is 5 d.

Gelatinization viscosity properties and expansion properties of fermented starch obtained from different types of starch are measured, and results are shown in Table 6 and Table 7. It is known from Table 6 and Table 7 that a peak viscosity of the potato starch is too high and reaches 4,890.5 mPa·s, a peak viscosity of the rice starch and a peak viscosity of the corn starch are too low and reach 678.0 mPa·s and 754.5 mPa·s respectively, and expansion properties of raw starch are all quite low. A viscosity of the potato starch obtained after fermentation is further reduced to 2,979.5 mPa·s, the fermented potato starch is likely to be endowed with an expansion property by prolonging a fermentation time, but it consumes time and expansive raw materials, which leads to low production economic benefits.

TABLE 6

Measurement of gelatinization viscosity properties of starch from different sources and obtained fermented starch

| Category | Peak viscosity (mPa · s) | Trough viscosity (mPa · s) | Breakdown value (mPa · s) | Final viscosity (mPa · s) | Setback value (mPa · s) |
|---|---|---|---|---|---|
| Potato starch | 4890.5 ± 218.5 | 1881.0 ± 39.6 | 3009.5 ± 178.9 | 2300.5 ± 31.8 | 419.5 ± 7.8 |
| Fermented potato starch | 2979.5 ± 38.8 | 1454 ± 29.7 | 1419.0 ± 72.1 | 2040.5 ± 34.6 | 480.0 ± 1.4 |

TABLE 6-continued

Measurement of gelatinization viscosity properties of starch from different sources and obtained fermented starch

| Category | Peak viscosity (mPa · s) | Trough viscosity (mPa · s) | Breakdown value (mPa · s) | Final viscosity (mPa · s) | Setback value (mPa · s) |
|---|---|---|---|---|---|
| Rice starch | 678.0 ± 8.49 | 380.5 ± 16.3 | 295.5 ± 7.8 | 832.5 ± 14.9 | 452.0 ± 1.4 |
| Fermented rice starch | 611.5 ± 0.7 | 483.5 ± 3.5 | 128.0 ± 2.8 | 643.0 ± 1.4 | 159.5 ± 5.0 |
| Corn starch | 754.5 ± 3.5 | 614.5 ± 10.6 | 140.0 ± 7.1 | 802.0 ± 21.2 | 185.0 ± 31.8 |
| Fermented corn starch | 729.5 ± 74.2 | 511.5 ± 47.4 | 218.0 ± 26.9 | 678.5 ± 55.9 | 167.0 ± 8.5 |

TABLE 7

Measurement of expansion properties of starch from different sources and obtained fermented starch

| Starch category | Potato starch | Fermented potato starch | Rice starch | Fermented rice starch | Corn starch | Fermented corn starch |
|---|---|---|---|---|---|---|
| Expansion property (mL/g) | 1.62 ± 0.09 | 1.52 ± 0.09 | 0.62 ± 0.03 | 1.31 ± 0.03 | 0.64 ± 0.02 | 0.93 ± 0.06 |

Comparative Example 1 Preparation of Fermented Tapioca Starch by Direct Artificial Acid Addition Production method: The production method comprises the steps: preparing 40% (w/w) tapioca starch and adding lactic acid to the starch for reaction for different times at a reaction temperature of 37° C., washing starch milk to a pH of 5 after reaction ends, adjusting a water content of a fermented tapioca starch basis to 50%, and flat spreading the starch milk with an adjusted water content on a drying container at an average illumination intensity of 150,000 lux for an illumination time of 8 h to obtain the fermented tapioca starch.

Results: The production time of the whole process is 2 d, and the expansion property of the obtained tapioca starch is poor.

Gelatinization viscosity properties of the fermented tapioca starch obtained from acid with different concentrations are measured, and results are shown in Table 8. It is found through experiments that by adding pure lactic acid with a same concentration (1%) to fermentation liquor, the viscosity of the starch may be rapidly reduced within a short time and meanwhile the expansion property of the starch is poor. By adjusting an acid concentration and processing time, the peak viscosity of the starch is within a proper range of 1,100-1,200 mPa·s, and it is found that the expansion property of the starch slightly changes, however, by a small increase amplitude. In conclusion, direct acid addition may shorten a fermentation time, but it fails to lead to an excellent expansion property.

TABLE 8

Measurement of gelatinization viscosity properties of fermented tapioca starch obtained from acid with different concentrations in Comparative example 1

| Category | Peak viscosity (mPa · s) | Trough viscosity (mPa · s) | Breakdown value (mPa · s) | Final viscosity (mPa · s) | Setback value (mPa · s) |
|---|---|---|---|---|---|
| 1%-24 h | 417.0 ± 8.5 | 68 ± 2.8 | 352.5 ± 10.6 | 101.0 ± 1.4 | 34.5 ± 0.7 |
| 0.5%-24 h | 572.5 ± 12.0 | 106.0 ± 2.8 | 466.5 ± 9.2 | 166.5 ± 3.5 | 60.5 ± 0.7 |
| 1%-0.5 h | 655 ± 14.1 | 106.0 ± 1.4 | 549.0 ± 12.7 | 166.0 ± 0.0 | 60.0 ± 1.4 |
| 0.25%-12 h | 1143.5 ± 29.0 | 379.5 ± 23.3 | 764.0 ± 5.7 | 580.5 ± 37.5 | 201.0 ± 14.1 |
| 0.25%-24 h | 1118.0 ± 19.8 | 314.5 ± 4.9 | 803.5 ± 24.7 | 487.0 ± 8.5 | 172.5 ± 3.5 |
| 0.2%-24 h | 1186.5 ± 19.1 | 356.5 ± 10.6 | 830.0 ± 8.5 | 549.0 ± 12.7 | 192.5 ± 2.1 |

Expansion properties of the fermented tapioca starch obtained from acid with different concentrations are measured, and results are shown in Table 9.

TABLE 9

| Measurement of expansion properties of fermented tapioca starch obtained in Comparative example 1 | | | | | |
|---|---|---|---|---|---|
| Inoculum size of strain (%) | | | | | |
| 1%-24 h | 0.5%-24 h | 1%-0.5 h | 0.25%-12 h | 0.25%-24 h | 0.2%-24 h |
| Expansion property (mL/g) | | | | | |
| 3.93 ± 0.20 | 3.74 ± 0.55 | 4.11 ± 0.29 | 3.58 ± 0.27 | 3.77 ± 0.28 | 4.57 ± 0.85 |

1%-24 h: 1% of a mass of starch milk participates in lactic acid reaction for 24 h; 0.5%-24 h: 0.5% of the mass of starch milk participates in lactic acid reaction for 24 h; 1%-0.5 h: 1% of the mass of starch milk participates in lactic acid reaction for 0.5 h; 0.25%-12 h: 0.25% of the mass of starch milk participates in lactic acid reaction for 0.5 h; 0.25%-24 h: 0.25% of the mass of starch milk participates in lactic acid reaction for 24 h; and 0.2%-24 h: 0.2% of the mass of starch milk participates in lactic acid reaction for 0.5 h.

Comparative Example 2 Preparation of Fermented Tapioca Starch from Fermentation Liquor Obtained by Natural Fermentation With reference to Example 1, a seed solution is replaced with the settled and centrifuged fermentation liquor which is prepared from 40% starch milk by natural fermentation for 4 d, and a corresponding culture medium is unprocessed water. Other conditions are not changed, and the fermented tapioca starch is prepared. The production time of the whole process is 10-14 d.

Gelatinization viscosity properties of the tapioca starch fermented by a multi-strain fermentation system are measured, and results are shown in Table 10. It is known from Table 10 that the fermented tapioca starch obtained by fermentation for 4 d has a peak viscosity of 1,160 mPa·s and a proper viscosity range of 1,100-1,200 mPa·s. It is known from Table 11 that the starch has a weak expansion property, which may be caused when amylase and other relevant substances generated by multi-strain fermentation complexly change the starch and thus cause a high final viscosity and increasing setback to the starch. It is known from Table 11 that after fermentation for 4 d, 6 d and 8 d, the expansion property of the starch rises first and then falls, but it is still poor compared with that of single-strain fermentation. After fermentation for 8 d, an obvious starch flocculation phenomenon is observed in an experiment, the peak viscosity falls, the final viscosity obviously rises, and the setback value also rises.

TABLE 10

| Measurement of gelatinization viscosity properties of fermented tapioca starch obtained by multi-strain fermentation system | | | | | |
|---|---|---|---|---|---|
| Fermentation time (d) | Peak viscosity (mPa · s) | Trough viscosity (mPa · s) | Breakdown value (mPa · s) | Final viscosity (mPa · s) | Setback value (mPa · s) |
| 4 | 1160.0 ± 113.1 | 672.5 ± 37.5 | 487.5 ± 75.7 | 1061.0 ± 69.3 | 388.5 ± 31.8 |
| 6 | 1080.5 ± 10.6 | 556.5 ± 7.8 | 524.0 ± 18.4 | 858.5 ± 17.7 | 302.0 ± 9.9 |
| 8 | 989.0 ± 2.8 | 738.5 ± 2.1 | 250.5 ± 4.9 | 1144.0 ± 7.1 | 405.5 ± 9.2 |

Expansion properties of the fermented tapioca starch obtained by a multi-strain fermentation system are measured, and results are shown in Table 11.

TABLE 11

Measurement of expansion properties of fermented tapioca starch obtained by multi-strain fermentation system in natural fermentation

| | Fermentation time (d) | | |
|---|---|---|---|
| | 4 | 6 | 8 |
| Expansion property (mL/g) | 4.05 ± 0.84 | 5.46 ± 0.32 | 4.27 ± 0.66 |

What is claimed is:

1. A method of preparing fermented tapioca starch for baking, comprising:
   mixing a carbon source with water to prepare a fermentation medium, wherein the carbon source is molasses, and wherein an initial mass concentration of the carbon source in the fermentation medium 1.0 g/100 g to 2.0 g/100 g;
   sterilizing the fermentation medium at a temperature of from 115° C. to 121° C. and a pressure of from 0.1 MPa to 0.3 MPa;
   adding tapioca starch to form tapioca starch milk; and
   fermenting the tapioca starch milk by adding an inoculum of *Lactobacillus plantarum* (*L. plantarum*) CCTCC M2017138 to the tapioca starch milk,
   wherein the inoculum comprises at least $4.2 \times 10^9$ CFU/mL *L. plantarum*,
   wherein the tapioca starch milk is first added to the inoculum in an amount of 50% of a mass of the fermentation medium, and then an inoculum size of 10% to 15% by mass of the tapioca starch milk is added to the tapioca starch milk.

2. The method according to claim 1, wherein a mass concentration of the tapioca starch in the tapioca starch milk is 30 g/100 g to 70 g/100 g.

3. The method according to claim 1, wherein fermenting is conducted at a temperature if 30° C. to 40° C., for 12 hours to 120 hours.

4. The method according to claim 2, wherein fermenting is performed at a fermentation temperature of 30° C. to 40° C., for 12 hours to 120 hours.

5. The method according to claim 1, further comprising: illuminating after fermenting.

6. The method according to claim 2, further comprising: illuminating after fermenting.

7. The method according to claim 3, further comprising: illuminating after fermenting.

8. The method according to claim 1, further comprising the following steps performed after fermenting:
   adjusting pH of the tapioca starch milk to pH 3.5 to 7;
   adjusting a water content of the tapioca starch milk basis to 30% to 60% by washing the tapioca starch milk;
   flat spreading the tapioca starch milk on a drying container; and
   exposing the tapioca starch milk to 100,000 to 300,000 lux illumination for 6 hours to 72 hours.

9. The method of claim 8, wherein the pH is adjusted to 5.0.

* * * * *